(12) United States Patent
Windt

(10) Patent No.: US 7,794,144 B2
(45) Date of Patent: Sep. 14, 2010

(54) OPTICAL ALIGNMENT SYSTEM AND ALIGNMENT METHOD FOR RADIOGRAPHIC X-RAY IMAGING

(75) Inventor: David L. Windt, New York, NY (US)

(73) Assignee: Reflective X-Ray Optics LLC, New York City, NY (US)

( * ) Notice: Subject to any disclaimer, the term of this patent is extended or adjusted under 35 U.S.C. 154(b) by 100 days.

(21) Appl. No.: 12/360,928

(22) Filed: Jan. 28, 2009

(65) Prior Publication Data
US 2009/0190722 A1   Jul. 30, 2009

Related U.S. Application Data

(60) Provisional application No. 61/062,459, filed on Jan. 28, 2008.

(51) Int. Cl.
*A61B 6/08* (2006.01)
*G01D 18/00* (2006.01)
(52) U.S. Cl. .......................... 378/206; 378/63; 378/207
(58) Field of Classification Search .................. 378/63, 378/206, 207
See application file for complete search history.

(56) References Cited

U.S. PATENT DOCUMENTS

| 5,031,203 | A | * | 7/1991 | Trecha ....................... 378/205 |
| 5,136,627 | A |   | 8/1992 | Conrads et al. |
| 5,241,578 | A | * | 8/1993 | MacMahon ................. 378/154 |
| 5,517,546 | A | * | 5/1996 | Schmidt ...................... 378/206 |
| 5,539,798 | A | * | 7/1996 | Asahina et al. ............. 378/98.5 |
| 5,644,616 | A | * | 7/1997 | Landi et al. ................. 378/206 |
| 6,267,502 | B1 | * | 7/2001 | McNeirney et al. ......... 378/206 |
| 6,339,636 | B1 |   | 1/2002 | Ogawa |
| 6,473,489 | B2 | * | 10/2002 | Bani-Hashemi et al. ....... 378/63 |
| 6,614,875 | B2 | * | 9/2003 | Suuronen ...................... 378/63 |
| 6,694,169 | B2 | * | 2/2004 | Kennedy et al. ............ 600/426 |
| 7,176,467 | B2 | * | 2/2007 | Sandrik et al. ......... 250/370.11 |
| 7,313,223 | B2 | * | 12/2007 | Unfors ...................... 378/98.8 |
| 7,490,986 | B2 | * | 2/2009 | Takekoshi et al. ........... 378/206 |
| 2005/0069092 | A1 |   | 3/2005 | Xiaodong et al. |
| 2006/0285646 | A1 |   | 12/2006 | Unfors |

OTHER PUBLICATIONS

International Search Report for PCT/US2009/03222, dated Aug. 12, 2009.

* cited by examiner

*Primary Examiner*—Edward J Glick
*Assistant Examiner*—Thomas R Artman
(74) *Attorney, Agent, or Firm*—Pryor Cashman LLP; Barry E. Negrin, Esq.

(57) ABSTRACT

An X-ray optical alignment system for X-ray imaging devices includes a visible-light point source and a multi-axis positioner therefor, fixedly mounted with respect to the X-ray focal spot. A mirror or beamsplitter is fixedly mounted with respect to the X-ray focal spot and disposed in the beam path of the X-ray source. The beamsplitter reflects light emitted from the light source and transmits X-rays emitted from the X-ray source. A first X-ray attenuating grid is fixedly but removably mountable with respect to the X-ray source, having a first X-ray attenuation pattern; and a second X-ray attenuating grid is adjustably mountable with respect to the first grid having a second X-ray attenuating pattern corresponding to the first X-ray attenuating pattern. When the grids are aligned, their attenuating patterns are also aligned and allow X-rays from the X-ray source and light reflected from the beamsplitter to pass therethrough.

25 Claims, 10 Drawing Sheets

SIDE VIEW

FRONT VIEW

SIDE VIEW

ISOMETRIC VIEW

OPTICAL ALIGNMENT SYSTEM AND ALIGNMENT METHOD FOR RADIOGRAPHIC X-RAY IMAGING

RELATED APPLICATIONS

Domestic priority is claimed from U.S. Provisional Patent Application No. 61/062,459 entitled "Optical Alignment System and Alignment Method for Radiographic X-Ray Imaging" filed Jan. 28, 2008, the entirety of which is incorporated by reference herein.

BACKGROUND OF THE INVENTION

1. Field of the Invention

The invention is directed to imaging systems, and more particularly to radiographic X-ray imaging systems, for medical, industrial, and other applications.

2. Description of Related Art

Radiographic X-ray imaging systems for medical, industrial and other applications typically use a point-source X-ray tube in which energetic electrons impinge upon a solid metal target thereby producing a cone-beam of X-ray light emanating from the focal spot. The spectrum of X-rays emitted from such tubes is poly-energetic, having line emission characteristic of the anode material used in the tube (commonly tungsten, or in the case of mammography, molybdenum or rhodium) superimposed on a broad continuum of Bremsstrahlung radiation extending to a high-energy cutoff determined by the applied voltage. For many imaging tasks, however, increased image contrast—and lower patient dose, in the case of medical applications—can be achieved using mono-energetic radiation.

One method for producing (nearly) mono-energetic radiation from electron-impact X-ray tubes utilizes multilayer X-ray mirrors to reflect and filter the X-ray light before it reaches the tissue or sample under study. [See, for example, 'X-ray monochromator for divergent beam radiography using conventional and laser produced X-ray sources', H. W. Schnopper, S. Romaine, and A. Krol, Proc. SPIE, 4502, 24, (2001)]. The X-ray mirrors include flat substrates coated with X-ray-reflective multilayer coatings that reflect X-rays only over a narrow energy band. The multilayer X-ray mirrors are positioned between the X-ray tube focal spot and the sample or patient. Because the mirrors only work at shallow grazing incidence angles, a single mirror will only yield a thin fan-beam of mono-energetic X-ray light. Thus, to produce mono-energetic light over a large field at the image plane, one of two approaches can be used. In the first approach, a single mirror is scanned over a wide angular range during the X-ray exposure. In the second approach, an array of stacked mirrors are used, constructed from a number of thin mirrors and spacers that are stacked together with high precision in a wedge shape: while each individual mirror will produce a narrow fan beam, the array of mirrors will collectively produce an array of co-aligned fan beams. In the second approach using a mirror stack, however, the illumination pattern will also include dark strips corresponding to the regions where the X-ray light is blocked by the edges of the mirrors. To compensate for the dark strips, the mirror stack can be scanned during exposure, similar to the way in which a single mirror is scanned in the first approach (albeit over a much smaller angular range), so that the bright and dark strips are averaged together to produce uniform illumination.

In any case, the requirements on positioning the mirrors relative to the focal spot are stringent: in particular, the angular position of each mirror must be such that the incidence angle of X-rays is controlled to a fraction of a degree. As an example, in the specific case of multilayer X-ray mirrors designed for mammography systems operating near 20 keV, approximately, typical grazing incidence angles are in the range of 0.3-0.7 degrees, while the angular acceptance angle of the narrow-band multilayer coating can be as small as 0.02 degrees; therefore the mirror must be positioned so that the error in graze angle is perhaps half of the acceptance angle, i.e., 0.01 degrees, or less. For other types of X-ray imaging systems utilizing higher-energy X-rays, the graze angles and acceptance angles are even smaller, and thus the requirements on alignment are even more stringent than for mammography.

For medical applications in particular, point-source X-ray systems generally incorporate a visible-light alignment system for patient registration, i.e., to ensure, by visual inspection of the optical illumination pattern, that the X-ray beam will illuminate the desired portion of the tissue under study. The visible-light alignment system is arranged to mimic the X-ray beam by implementing a small incandescent light bulb positioned at a virtual focal spot location, with the light emitted from the bulb reflecting off a 45-degree mirror (having low X-ray attenuation) positioned in the X-ray beam. [See, for example, 'The Essential Physics of Medical Imaging, $2^{nd}$ Edition', J. T. Bushberg, J. A. Seibert, E. M. Leidholdt, Jr., and J. M. Boone, Lippincott Williams & Wilkins publishers, Philadelphia, 2002, FIGS. 5-18, pg. 115.]

A visible light alignment system still can be used for patient registration when X-ray mirrors are implemented in a radiographic X-ray imaging system as outlined above: provided the visible-light is sufficiently co-aligned with the X-ray light, the visible light will reflect from the mirrors and accurately illuminate the image field, just as it does in conventional systems. The same visible light alignment system could also be used to align the mirrors themselves, in principle, which is an otherwise difficult task, again provided that the visible/X-ray misalignment is sufficiently small. U.S. governmental regulations relating to radiographic X-ray imaging systems (21 CFR §1020.31) require that the visible light field and X-ray field at the image plane be co-aligned such that the sum of the misalignments, along either the length or width of the field, is less than 2% of the distance from the X-ray focal spot to the image plane. While the misalignments permitted under governmental regulations are adequate for patient registration, such misalignments are completely inadequate for use with the X-ray mirrors designed to produce mono-energetic radiation that operate a relatively shallow grazing incidence angles: i.e., when X-ray mirrors are placed in the X-ray beam, the typical misalignments between the visible and X-ray beams in a conventional alignment system will make it difficult or impossible to use the visible beam to align the X-ray mirrors. Additionally, conventional visible-light alignment systems do not provide sufficiently precise adjustments of the position of the visible light source relative to the virtual focal point, and furthermore, the size of the light-emitting region itself is large relative to the X-ray focal spot size. Thus, conventional visible light systems are generally inadequate for use when X-ray mirrors are implemented.

In order to utilize a visible-light alignment system that is similar in concept to the systems currently in use, either for patient registration or to align X-ray mirrors implemented for mono-energetic radiation, an optical system with significantly increased precision is required. Furthermore, for precise optical alignment of the X-ray mirrors, the visible-light optical system must use a visible light point source having a focal spot whose size is equal to or smaller than the X-ray tube focal spot size. Finally, also required is an apparatus and a methodology for precisely co-aligning the visible and X-ray light cone-beams.

SUMMARY OF THE INVENTION

The present invention includes, respectively: (a) a precision optical system for use as a visible-light alignment system to be incorporated into radiographic X-ray imaging systems having a point-source X-ray tube (and preferably) utilizing X-ray mirrors), (b) a complementary alignment apparatus used to precisely co-align the visible and X-ray beams, and (c) a method for using these systems. The main components of the precision optical system are a fiber-coupled laser module, a multi-axis fiber optic positioner, and a mirror, for example, a reflective, optically-flat pellicle beamsplitter, having very low X-ray attenuation. The complementary alignment apparatus includes a set of matched X-ray attenuating metal alignment grids, a two-axis translation stage for precisely positioning the top grid relative to the bottom grid in the X-ray beam along two orthogonal directions, and a removable, precision mounting bracket to provide a method for installing the alignment grids with sufficient precision and repeatability. The method for using these systems describes how the optical alignment system and the set of alignment grids are implemented to ensure precise co-alignment of the visible and X-ray cone beams. The present invention is aimed specifically at mammographic applications, however it can apply equally well to all other medical and industrial radiographic X-ray imaging applications.

In one embodiment, the invention is an X-ray optical alignment system for X-ray imaging devices utilizing a point-source X-ray tube having an X-ray focal spot (and optionally utilizing X-ray mirrors for beam filtration). A visible-light point source is provided, as is a multi-axis positioner, coupled to the light source and fixedly mounted with respect to the X-ray focal spot. The multi-axis positioner enables spatial and angular adjustment of the visible-light point source. A mirror is fixedly mounted with respect to the X-ray focal spot and disposed in the beam path of the X-ray source, reflecting light emitted from the visible-light point source and transmitting X-rays emitted from the X-ray source. Preferably, the mirror is a beamsplitter, more preferably a pellicle beamsplitter. A first X-ray attenuating grid is fixedly but removably mountable with respect to the X-ray source and has a first X-ray attenuation pattern. A second X-ray attenuating grid is adjustably mountable with respect to the first grid and has a second X-ray attenuating pattern corresponding to the first X-ray attenuating pattern. When the first and second grids are aligned, the first and second attenuating patterns are also aligned and thereby allow X-rays from the X-ray source and light reflected from the mirror to pass therethrough.

Preferably, the visible-light point source includes a laser module coupled with an optical fiber. The multi-axis positioner is preferably an optical fiber positioner coupled to an emitting end of the optical fiber and enabling positional adjustment of the emitting end. The optical fiber is preferably a single mode optical fiber. The multi-axis positioner is preferably adjustable along three orthogonal translation directions, and in two orthogonal angular directions. A locking mechanism may be coupled to the multi-axis positioner to fix the position of the visible-light point source with respect to the X-ray focal spot.

A rigid mounting plate is preferably provided, fixedly attached to the X-ray imaging device, upon which the multi-axis positioner and the mirror/beamsplitter are fixedly mounted.

The second X-ray attenuating grid is preferably adjustable in the X-Y plane of the second grid. A locking mechanism is preferably provided to fix the position of the second grid in the X-Y plane. The second grid is adjustable in the X-Y plane, but it is fixed a preset Z distance from the first grid orthogonal to the X-Y plane. The dimensions (D) of features in the first and second attenuating patterns, D1 and D2, respectively, preferably correspond via the equation D1=Z1/Z2*D1 The first and second grids are preferably attached to a common bracket removably but fixedly securable to the X-ray imaging device.

The inventive optical alignment system also includes an X-ray detector—either film or electronic (digital)—positionable below the first and second grids, adapted to detect a resultant pattern of X-rays transmitted through the first and second grids from the X-ray source. In addition, the alignment system may also include one or more electronic visible light detectors, positionable below the first and second grids, adapted to detect a resultant intensity pattern of visible light transmitted through the first and second grids from the mirror/beamsplitter. A computer controller may be provided, coupled to an electronic X-ray detector and/or visible light detector(s). If it is coupled to the X-ray detector, the controller can automatically control the position of the second grid based on the X-rays detected by the detector. If it is coupled to the visible light detector(s), the controller can automatically control the position of the visible-light point source based on the visible light detected by the detector. In both cases, the computer can control the positions of the adjustable grid and/or the light source by detecting the resultant X-ray or visible light intensity patterns, e.g., overall brightness, pattern matching, or by some other manner.

The invention also includes a method for aligning a visible light alignment system and an X-ray imaging system of an X-ray imaging device, where the X-ray imaging system utilizes a point-source X-ray tube having an X-ray focal spot and optionally X-ray mirrors for beam filtration, and the visible light alignment system has a visible light point source. First, two X-ray attenuating alignment grids are fixedly attached a first distance apart from each other and a second distance apart from the X-ray focal spot, each grid having an attenuation pattern formed respectively therethrough to selectively block both X-rays and visible light. Next, a pattern of the X-rays from the X-ray source that pass through both alignment grids is detected. The relative misalignment of the two alignment grids based on the resultant detected X-ray pattern is determined and compared to the attenuation patterns of the two grids. The position of one of the grids is adjusted relative to the other grid so as to eliminate discrepancies between the detected X-ray pattern and the attenuation patterns of the grids. When the recorded X-ray pattern is substantially identical to the attenuation grid patterns after iterating these last two steps, the visible light source is activated, and relative misalignment of the two alignment grids and the visible light source are determined based on the resultant visible light pattern transmitted through the two grids. Finally, the position of the visible light source is adjusted so as to eliminate discrepancies between the transmitted visible light pattern and the attenuation patterns of the grid.

The X-ray detection step and associated adjustment of one of the grids can be performed manually. However, in such case, there must be some form of recording device used to record the resultant X-ray pattern (since the eye cannot see X-rays). The adjustment of the visible light source may also and more easily be performed manually, in which case no recording device (other than the eye) would be required. Optionally, however, one or more electronic visible light detectors may be used to detect the resultant visible light intensity pattern. Additionally, an electronic X-ray detector may be provided to detect the resultant X-ray pattern, and the adjustment of the grid may be performed automatically based on the resultant X-ray pattern detected by the electronic X-ray detector. Similarly, the adjustment of the position of the light source may be performed automatically based on the resultant visible light intensity pattern detected by the visible light detector.

DETAILED DESCRIPTION OF THE INVENTION

Figure 1A:
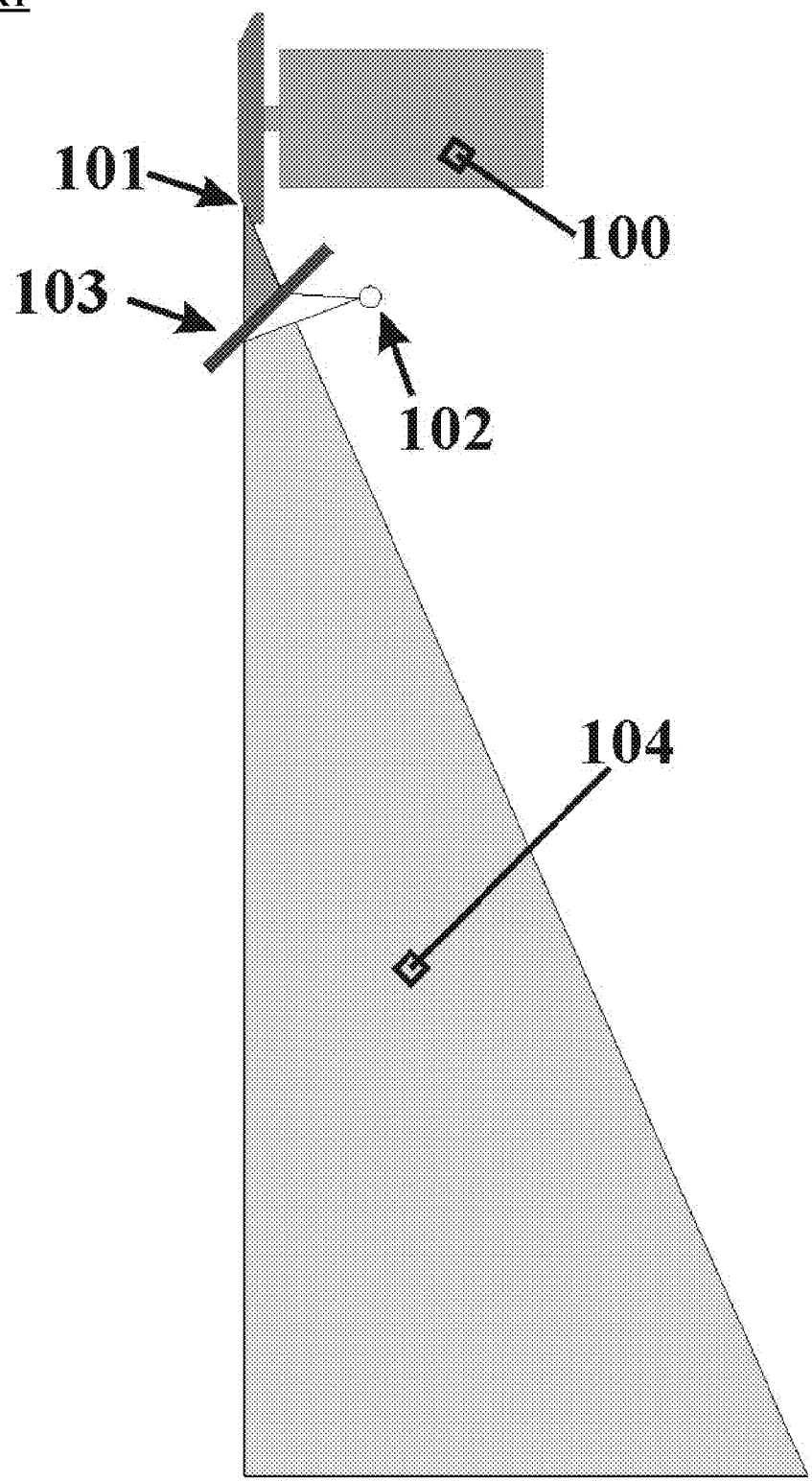
FIG. 1a is a schematic diagram showing a conventional radiographic X-ray imaging system including an X-ray tube with the X-ray cone-beam emanating from the focal spot, and a visible-light alignment system including an incandescent light source and a 45-degree mirror.

A conventional visible-light alignment system (FIG. 1a) commonly used in radiographic X-ray imaging systems includes an incandescent light bulb (102) and a 45-degree mirror (103) mounted in a fixed position relative to a point-source X-ray tube (100). The light bulb (102) is positioned at a virtual focal spot defined by the actual X-ray focal spot (101) and the angle and location of the 45-degree mirror relative to the X-ray spot. The visible-light cone beam overlaps with the X-ray cone beam (104), thereby providing a method for visual observation of the X-ray field at the object and/or image plane.

Figure 1B:
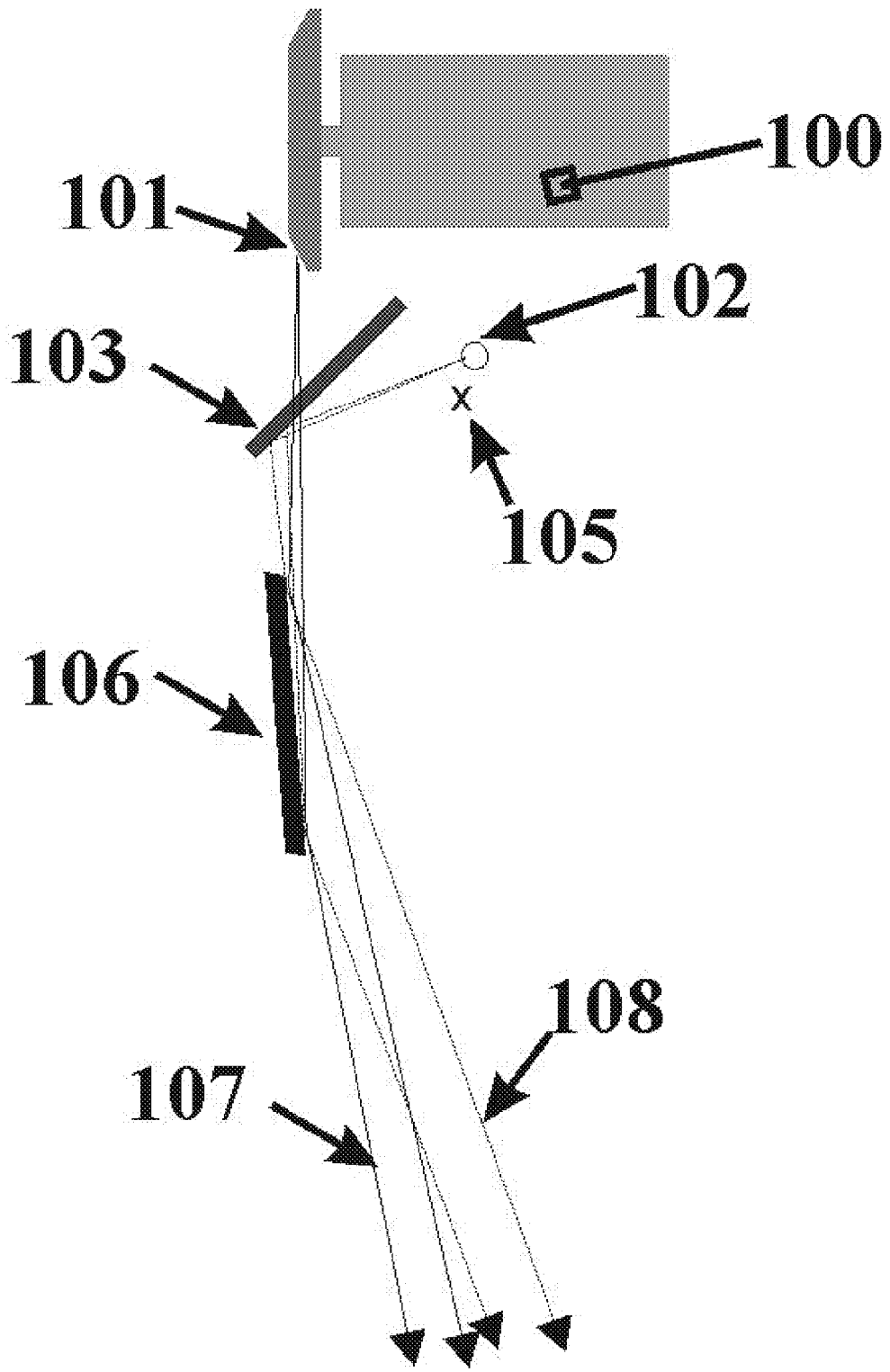
FIG. 1b shows a radiographic X-ray imaging system (including the alignment system of FIG. 1a) incorporating a grazing incidence multilayer X-ray mirror.
Figure 1C:
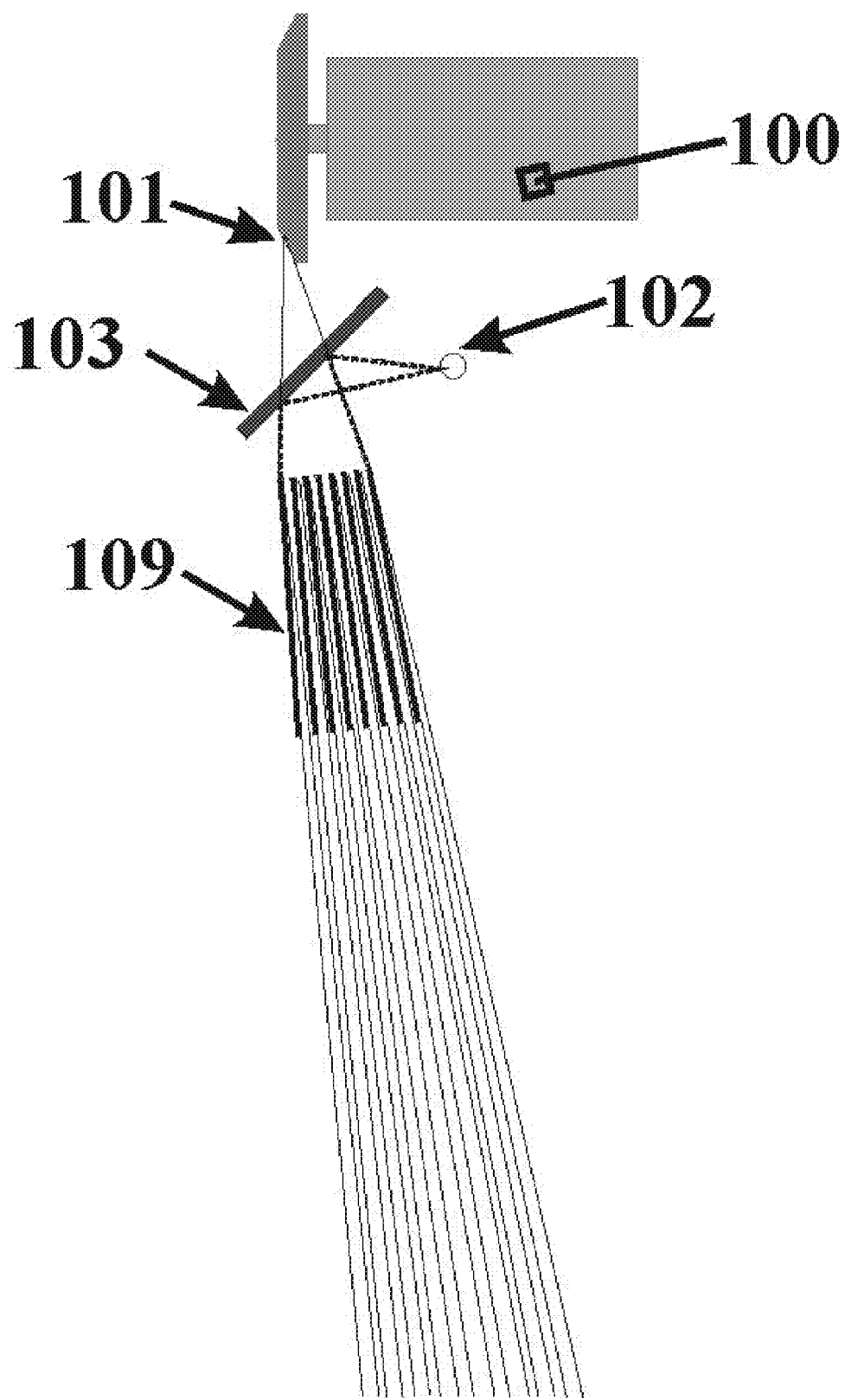
FIG. 1c shows a radiographic X-ray imaging system incorporating a stacked array of grazing incidence multilayer X-ray mirrors.
Figure 2:
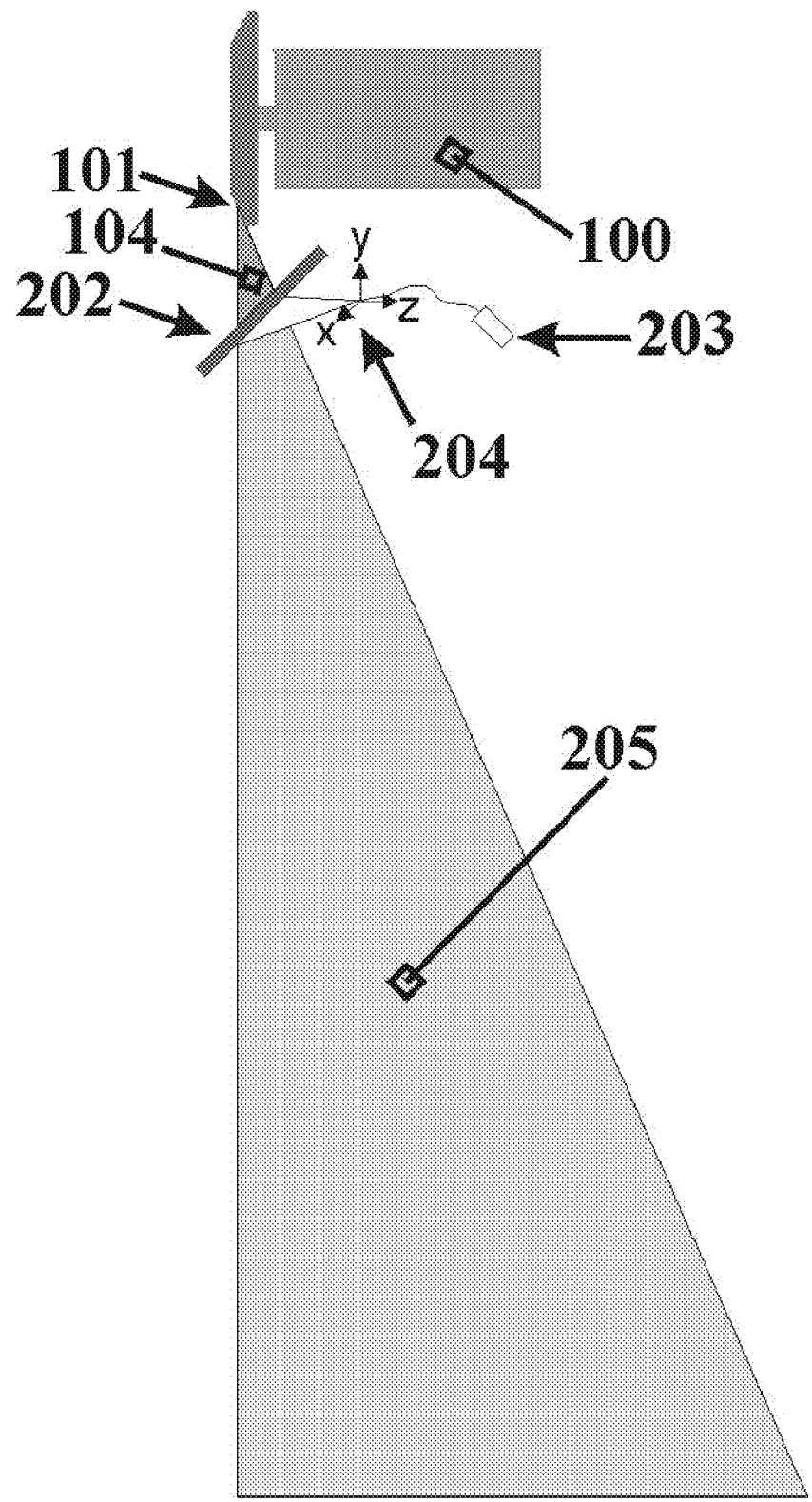
FIG. 2 is a schematic diagram showing an X-ray tube with the X-ray cone-beam emanating from the focal spot, and a precision optical alignment system in accordance with the invention, including a fiber-coupled laser module, a fiber positioner, and a pellicle beamsplitter.

A radiographic X-ray imaging system incorporating a single multilayer X-ray mirror for beam filtration is shown in FIG. 1b. The X-ray mirror (106) must be precisely positioned in the X-ray beam. A virtual focal spot (105) is determined by the position and angle of the 45-degree mirror (103) relative to the X-ray spot. When the light source (102) used in the visible alignment system is displaced from the position of the virtual focal spot (105), as in FIG. 1b, then visible rays (108), shown as dashed lines, will impinge upon the X-ray mirror at incidence angles that are different from those of the X-rays. Thus, the directions of the reflected visible light rays will be different than the directions of the reflected X-rays, and the reflected visible light rays that reach the image plane will be spatially displaced from the positions of the X-rays in the image plane. It is clear from FIG. 1b that the visible light alignment system cannot be used to precisely adjust the position and angle of the X-ray mirror unless the visible light source (102) is sufficiently coincident with the virtual focal spot (105). The same constraints on the visible alignment system apply as well to the case of a radiographic X-ray imaging system that uses two or more X-ray mirrors; FIG. 1c shows a system incorporating a stack of X-ray mirrors arranged into a wedge-shaped array.

Description of the invention will now be given with reference to FIGS. 2-6. It should be understood that these figures are exemplary in nature and in no way serve to limit the scope of the invention, which is defined by the claims appearing hereinbelow.

The present invention provides an optical system for use as a visible-light alignment system to be incorporated into X-ray imaging systems utilizing X-ray mirrors for medical, industrial or other radiographic applications, that has substantially greater precision relative to conventional visible-light registration systems. The main components of the precision optical system (FIGS. 2 & 3) are a fiber-coupled laser module (203), a multi-axis fiber optic positioner (204), and a reflective, optically-flat pellicle beamsplitter (202). All three components are commercially available from a variety of suppliers (Edmund Optics of Barrington, N.J.; Newport Corporation, of Irvine, Calif., etc.).

The laser light emerging from the polished end of the optical fiber (306) of module 203 diffracts into a spherical wave (i.e., a cone beam (307)) with very low wavefront distortion, and thus serves as a point source of visible light that can be made to overlap the X-ray beam (205). The fiber optic positioner (204) is used to locate the emitting end of the fiber at a virtual focal spot position with micron-level precision along three orthogonal axes. The end of the single-mode fiber (306) itself is typically only a few microns in diameter, which is considerably smaller than typical X-ray focal spot sizes; the X-ray tubes used for mammography, for example, commonly have a fine focus of 100 microns. The fiber end is also much smaller than the size of the light-emitting region in a typical incandescent light bulb used in conventional visible alignment systems; the emitting spot in an incandescent light bulb is also too large to use for precise mirror alignment.

The visible laser-light cone-beam (307) reflects from the optically-flat pellicle (202), which is preferably made of a thin (of order 5 microns) polymer membrane coated with a thin metal layer, such as aluminum, for high reflectance at the laser wavelength. The laser can be of any visible light wavelength but is preferably in the green (approx. 510 nm.) The membrane is stretched over a rigid frame to achieve optical flatness: the reflecting optical surface of the pellicle is flat to better than 600 nm per mm, typically. Because the pellicle (202) is so thin, X-ray attenuation is almost negligible, yet the optical surface of the pellicle (202) can be comparable to conventional polished glass flat mirrors which are otherwise unsuitable because they would cause too much X-ray attenuation. (In conventional visible-light alignment systems, a simple flat mirror is used, commonly being made from metallized plastic. The optical quality of such a mirror is far too poor to use for precise X-ray mirror alignment, however, as the resulting distortions in the reflected wavefront would cause the effective size of the visible light point source to be too large.) The pellicle (202) is positioned in the X-ray beam (104) at an angle near 45 degrees, approximately. The fiber positioner (204) also provides for two axes of rotation, so that the visible beam can be centered relative to the X-ray beam. The fiber positioner may include locking mechanisms (204A) (see FIG. 3C) to prevent adjustment of the fiber position once the system has been aligned, as described below.

The optical system is rigidly attached to an optical alignment system mounting plate (303) that has been machined to accommodate mounting the pellicle (202), the fiber positioner (204), and the laser module (203). Alternatively, the fiber-coupled laser module can be mounted remotely, because it is only the position of the end of the fiber that is important. The optical alignment system mounting plate also includes mounting holes for attachment to the X-ray tube mounting bracket (302), thereby ensuring a precise, stable platform for mounting the optical components relative to the X-ray focal spot (101). Also included are mounting holes for a collimating aperture (315), needed to limit the size of the X-ray beam to match the object being imaged.

Figure 3A:
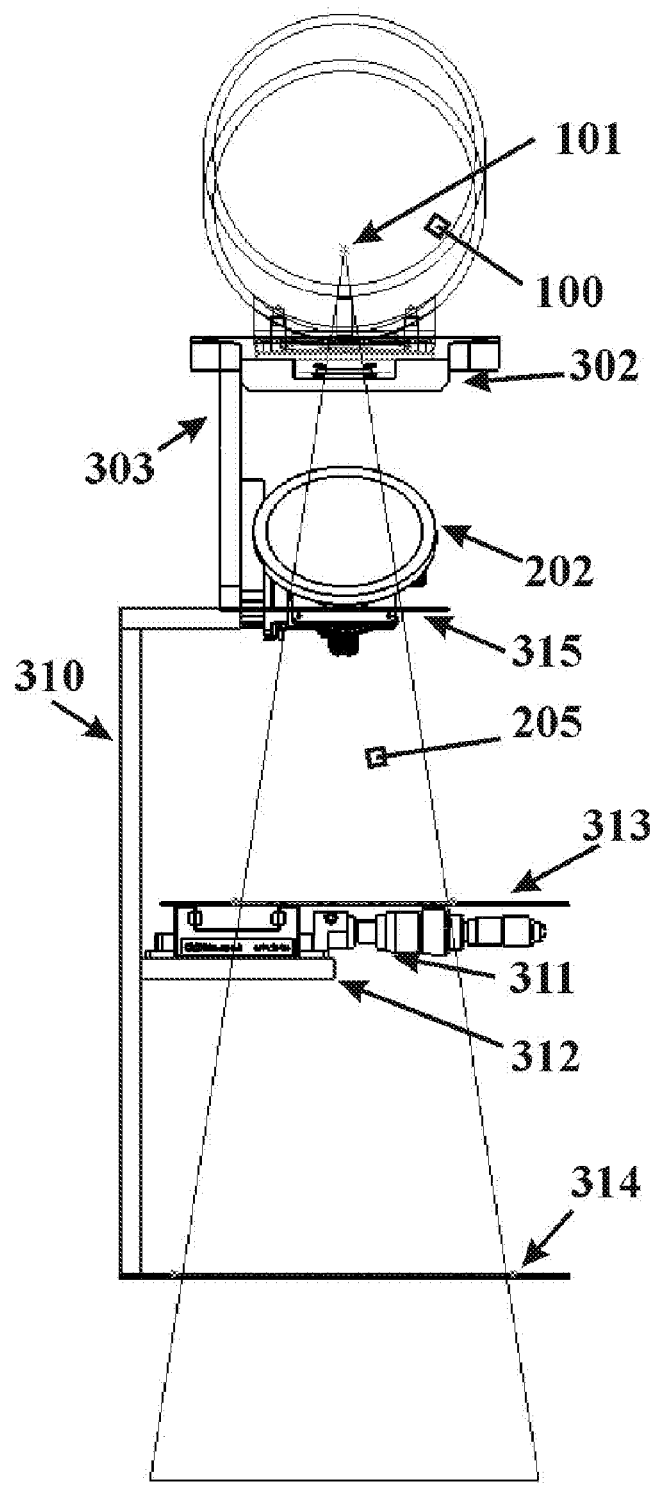
FIGS. 3A-C are front elevation, side elevation, and perspective views showing the same components shown in FIG. 2 along with a complementary alignment apparatus in accordance with the invention, including two metal alignment grids, an X-Y translation stage to precisely position the alignment grids, and a removable alignment grid mounting bracket.
Figure 3B:
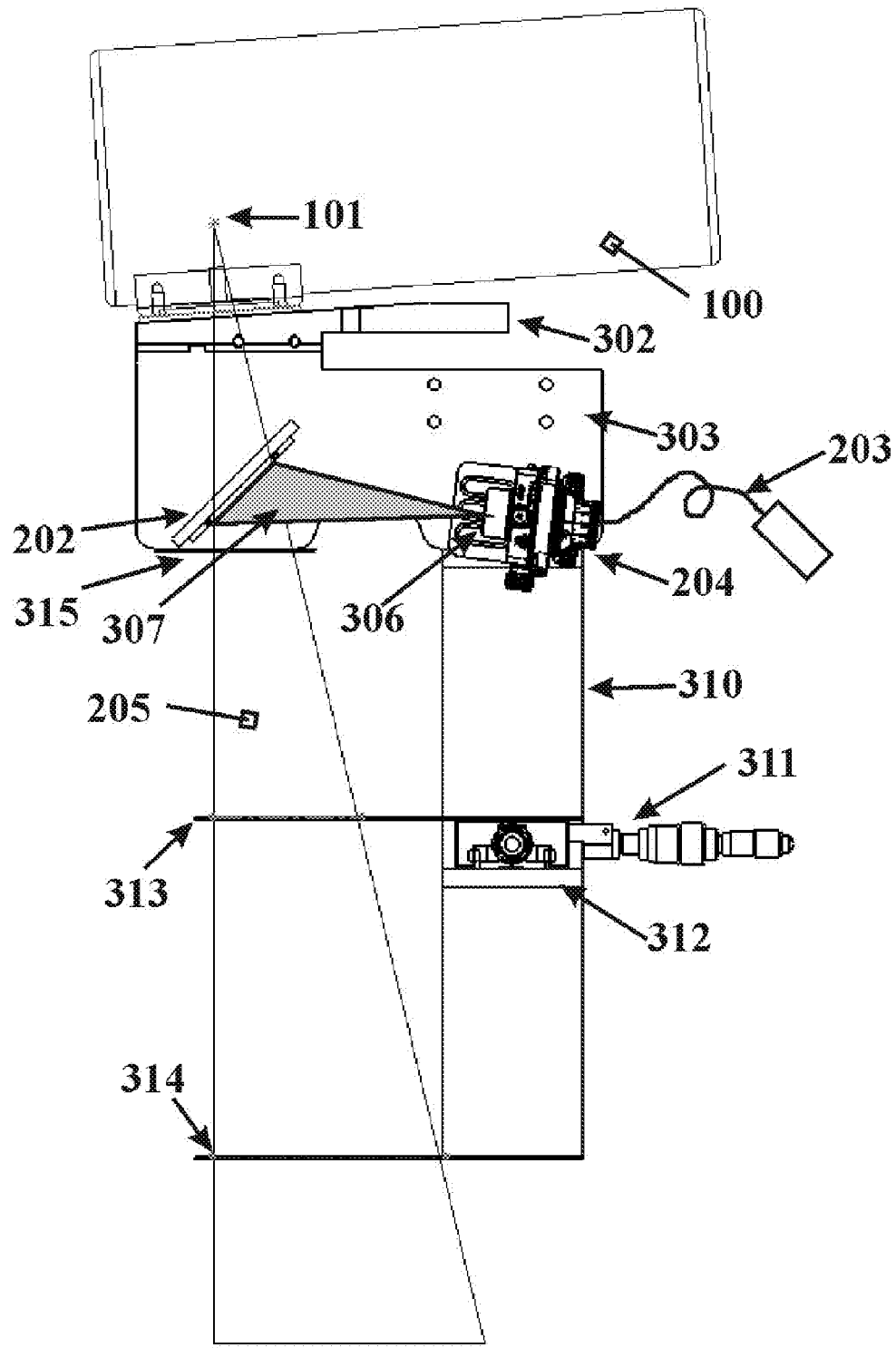
Figure 3C:
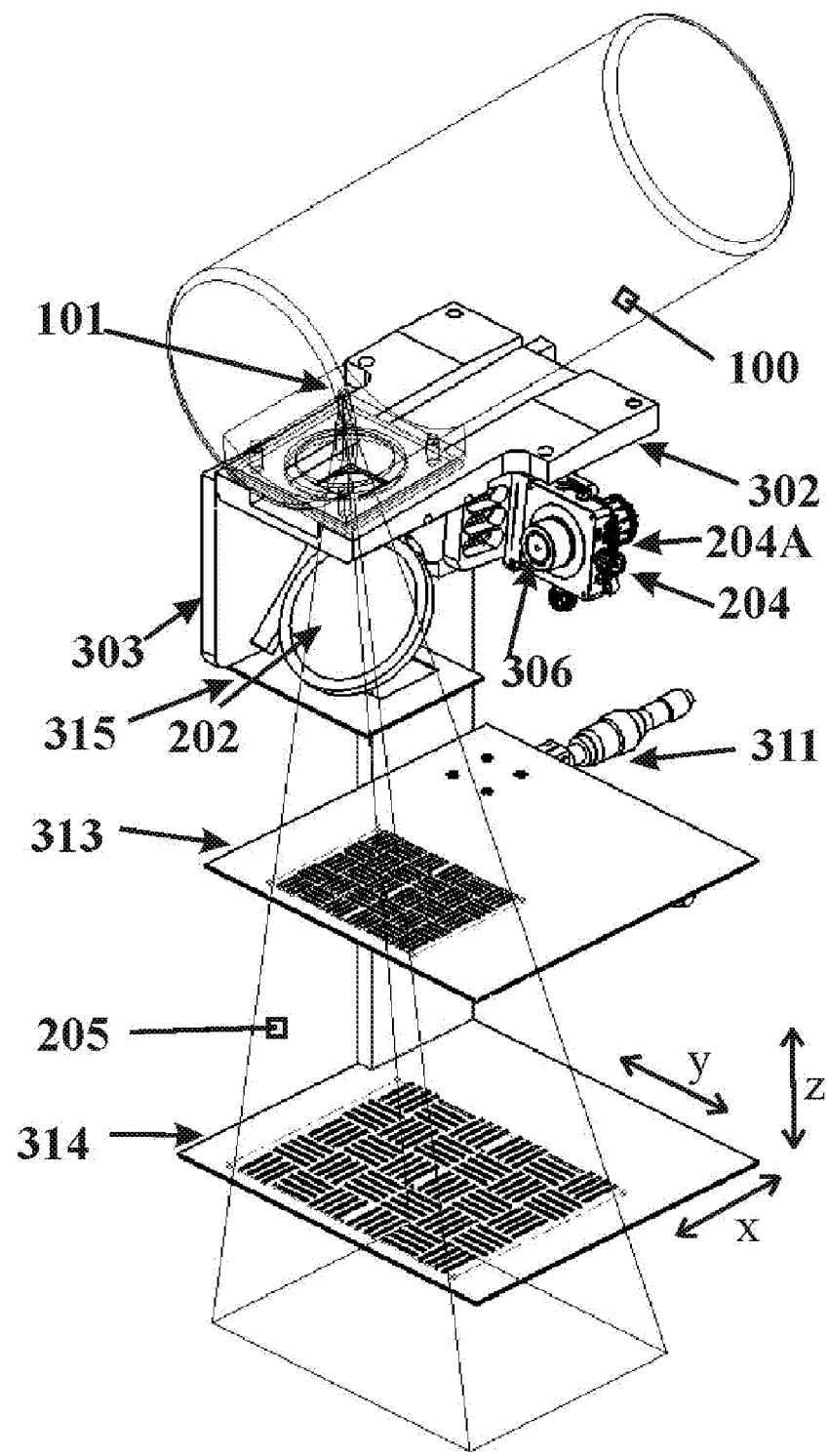
Figure 4:
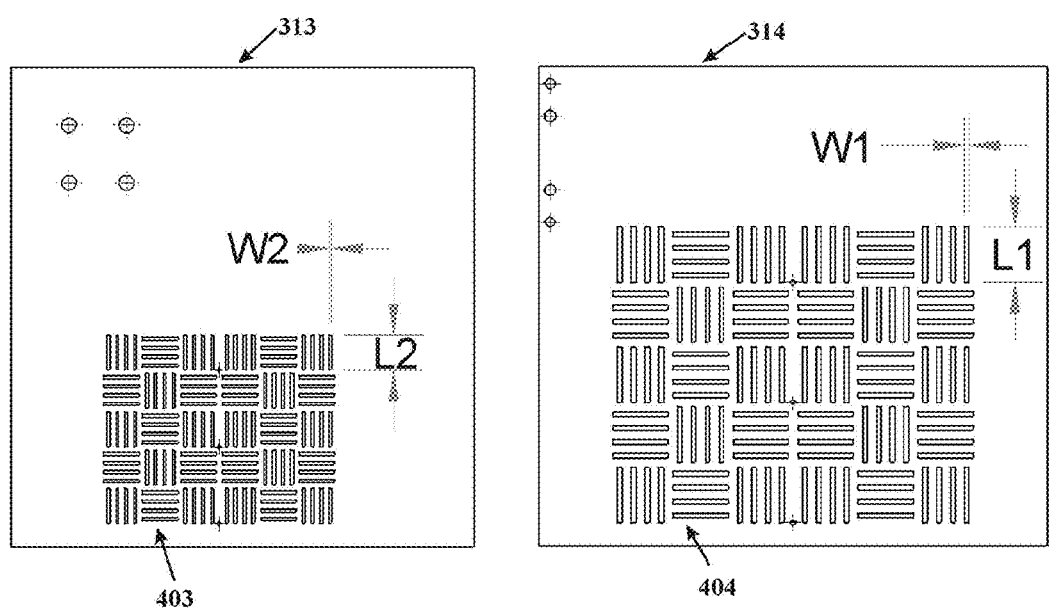
FIG. 4 is a top elevation view of an example of a pair of corresponding alignment grids in accordance with the invention.
Figure 5:
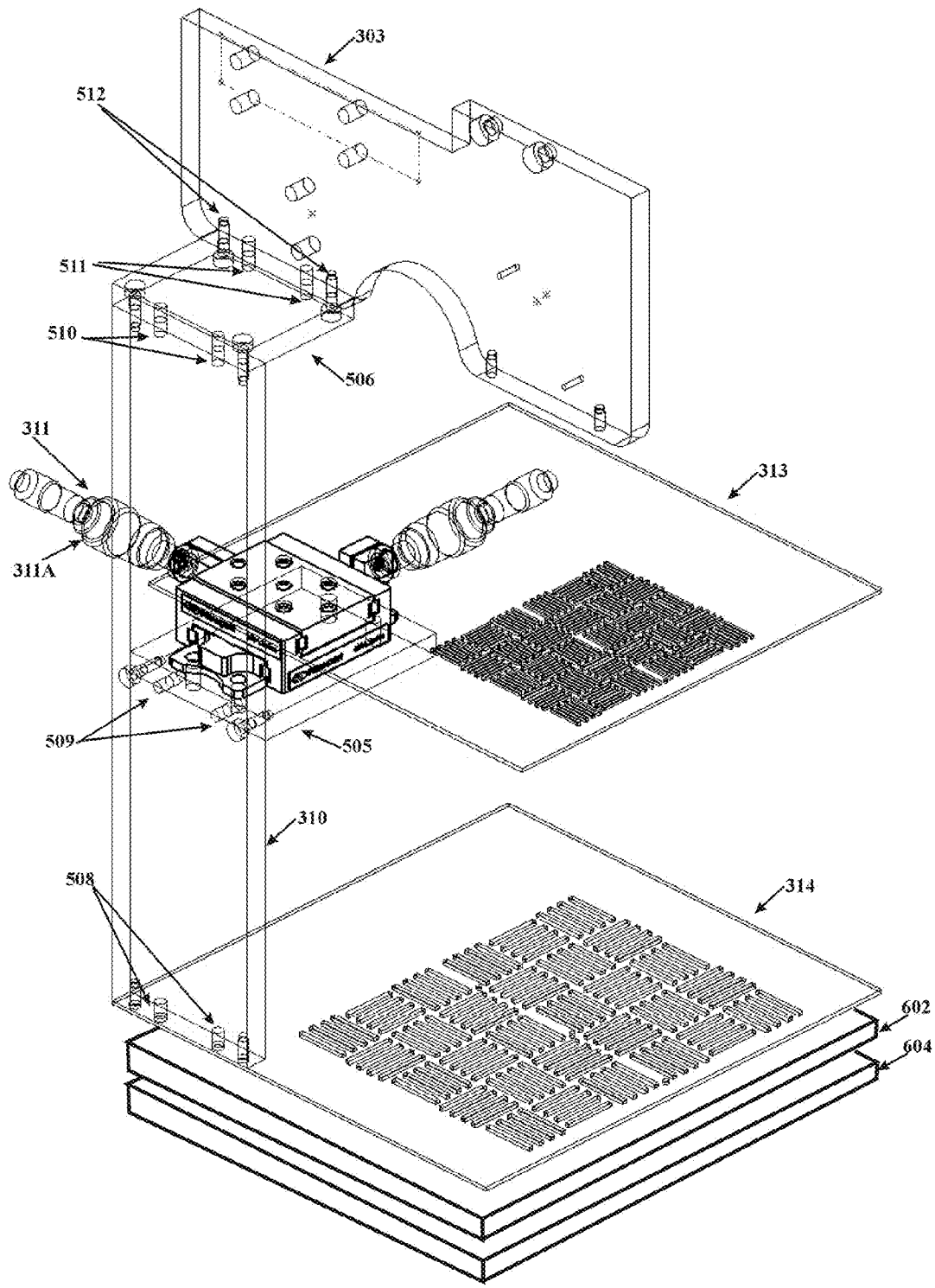
FIG. 5 is a perspective view showing the alignment grids, the X-Y translation stage used to position the top grid, and the alignment grid mounting bracket, all in accordance with the invention.

The present invention also provides a complementary alignment apparatus (FIGS. 3, 4 and 5) used to precisely co-align the visible and X-ray beams. The inventive alignment apparatus includes a set of matched X-ray attenuating metal grids (313, 314), a two-axis translation stage (311) for precisely positioning the top grid (313) relative to the bottom grid (314) in the X-ray beam, and a removable, precision mounting bracket (310) to provide a mechanism for installing the alignment grids with sufficient repeatability. The two alignment grids (313) and (314) both contain the same pattern of open spaces (403, 404), however the pattern formed in the 'top' grid must be scaled down in size relative to the 'bottom' grid by an amount that depends on the distances of the grids to the X-ray focal spot. That is, if the distance from the focal spot to the top grid is Z2, and the distance from the focal spot to the bottom grid is Z1, then a rectangular slot (FIG. 4) in the top grid (313) of width W2 and length L2 must have a corresponding slot in the bottom grid (314) of width W1 and length L1, where W1=Z1/Z2*W2, and L1=Z1/Z2*L2. There is great flexibility in the choice of the pattern of openings formed in the grids, provided that (a) the pattern of openings spans the entire illuminated area, and (b) the pattern is sensitive to misalignments in both orthogonal directions X and Y. An example set of alignment grids having an array of horizontal and vertical slots is shown in FIGS. 3, 4, and 5. Other suitable grid patterns include a "bulls eye" pattern including concentric circular slots, a "star" pattern having radial, tapered slots, or any combination of such patterns, similar to resolution test patterns commonly used to check optical system performance. A general equation covering any such pattern element, rectangular or not, can be expressed as D1=Z1/Z2*D2, where D1 is the feature dimension in the bottom grid and D2 is the corresponding feature dimension in the top grid.

The patterned alignment grids can be fabricated into metal plates having sufficient X-ray attenuation for the X-ray energies in use. Fabrication of the grid patterns can be achieved using conventional machining, chemical etching, or any other suitable method. One preferred embodiment utilizes alignment grids made of machined brass plates of order 1 to 2 mm in thickness. In another preferred embodiment, the grids are made of tantalum sheet of order 0.5 mm in thickness, that have been lithographically patterned and then chemically etched (see, for example, Fotofab, 3758 W. Belmont Ave., Chicago, Ill. 60618.)

The two alignment grids are mounted to the alignment grid mounting bracket assembly (310, 505, 506), which is fabricated so that the two grids are separated from the X-ray focal spot by precisely defined distances in the Z direction. Precision dowel pins (508, 509, 510, 511) are used throughout for registration. The bottom grid (314) is attached rigidly to the side plate of mounting bracket (310) using screws and dowel pins (508), while the top grid (313) is attached to a two-axis X-Y translation stage (311) that is itself attached to the mounting bracket side plate (310) via the mounting bracket X-Y plate (505). The translation stage enables micron-precision alignment in two directions of the top grid relative to the bottom grid. Locking actuators or locking stages (311A) can be used to prevent adjustment of the position of the top grid once the grids have been aligned to the X-ray beam, following the procedure described below. The alignment grid mounting bracket assembly attaches rigidly to the optical alignment system mounting plate (511): screws (512) hold the bracket assembly to the mounting plate (303), and precision dowel pins (511) are used to ensure that the mounting bracket assembly can be repeatedly removed and re-attached with sufficient precision so as to not disturb the alignment of the grids relative to each other and to the X-ray tube focal spot.

Figure 6:
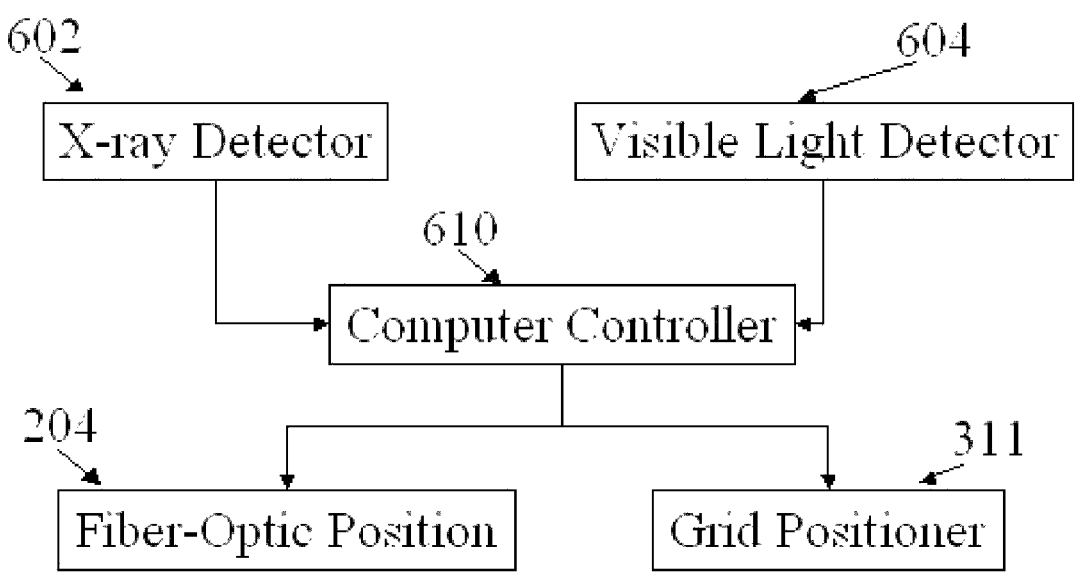
FIG. 6 is a schematic of a computer controller automatically controlling the position of the X-Y translation stage and/or the optical fiber positioner in accordance with the invention.

An optional component of the alignment apparatus is one or more electronic visible-light detectors, including imaging detectors, that can be used to precisely detect and/or measure the visible-light transmission through the two alignment grids over the image field. An exemplary such visible light detector (604) is shown in FIG. 5 below lower grid (314) and X-ray detector (602). As shown in FIG. 6, a computer controller (610) may be provided in communication with one or both of X-ray detector (602) and visible light detector (604). Computer controller (610) can use the information from these detectors to control the position of the movable top grid (313) by controlling the position of the X-Y translation stage (311) and the position of the end of the optical fiber by controlling fiber positioner (204). Computer controller (610) may base its decision for optimal placement of these components based on the detected intensity pattern of X-rays or visible light, respectively. Other possible mechanisms of automating the positioning of grid (313) and the visible light source are contemplated as being within the scope of the invention.

The present invention provides a method for precise co-alignment of the visible and X-ray cone beams. First, the visible-light alignment system is assembled and attached to the X-ray tube mounting plate (303) as in FIG. 3. Second, the alignment grids (313) and (314) are attached to the alignment grid mounting bracket assembly (310) as in FIG. 5, using a precision straight edge or surface plate to ensure that both orthogonal edges of the two grids are parallel. Third, the alignment grid mounting bracket assembly is attached to the optical alignment system mounting plate (303) as in FIG. 3. Fourth, an X-ray exposure is made using either X-ray film or a digital X-ray imaging detector (602) to record the resultant pattern, which is used to determine the relative misalignment of the two alignment grids. Fifth, based on the X-ray image results, the top alignment grid is translated in the X and/or Y directions using the alignment grid translation stage; the direction and magnitude of these translations are determined from the imaging results. This fifth step can be performed manually or automatically, as described above. Sixth, the fourth and fifth steps are repeated as necessary, until the misalignment between the two grids is below the spatial resolution of the X-ray imaging system in use. For mammography, for example, the effective spatial resolution of film-screen and full-field digital systems is of order 25 microns, and thus the two alignment grids can be co-aligned relative to the X-ray beam with an accuracy of 25 microns or less. Seventh, the laser module (203) is turned on, and the fiber positioner (204) is used to center the visible beam on the alignment grids (313) and (314), and to translate the light-emitting end of the fiber in three orthogonal directions so that the light passing through the top alignment grid is co-aligned with the apertures in the bottom grid. When properly aligned, either manually or automatically, the resultant emerging pattern of light in the image plane below the bottom grid (314) is uniform and identical to the X-ray image over the entire image field, as determined by either visual or electronic (using the optional electronic detectors) inspection. This ensures that the visible and X-ray beams are precisely co-aligned. Once the alignment is completed the alignment grid assembly is removed, by detaching the alignment grid mounting bracket from the optical alignment system mounting plate, for normal operation of the X-ray imaging system. Subsequent periodic checks of alignment are made by re-installing the alignment grid assembly as needed.

Having described certain embodiments of the invention, it should be understood that the invention is not limited to the above description or the attached exemplary drawings. Rather, the scope of the invention is defined by the claims appearing herein below and any equivalents thereof as would be appreciated by one of ordinary skill in the art.

What is claimed is:

1. An optical alignment system for X-ray imaging devices utilizing a point-source X-ray tube having an X-ray focal spot, comprising:
   a visible-light point source;
   a multi-axis positioner, coupled to said visible-light point source and fixedly mounted with respect to the X-ray focal spot, adapted to enable positional adjustment of said visible-light point source;
   a mirror fixedly mounted with respect to the X-ray focal spot and disposed in the beam path of the X-ray source, reflecting light emitted from said visible-light point source and transmitting X-rays emitted from the X-ray source;
   a first X-ray attenuating grid fixedly but removably mountable with respect to the X-ray source having a first X-ray attenuation pattern; and
   a second X-ray attenuating grid adjustably mountable with respect to said first grid having a second X-ray attenuating pattern corresponding to said first X-ray attenuating pattern,
   wherein when said first and second grids are aligned, said first and second attenuating patterns are also aligned and thereby allow X-rays from the X-ray source and light reflected from said mirror to pass therethrough.

2. An optical alignment system according to claim 1, wherein said visible-light point source comprises a laser module coupled with an optical fiber, wherein said multi-axis positioner comprises an optical fiber positioner coupled to an emitting end of said optical fiber and enabling positional adjustment of said emitting end.

3. An optical alignment system according to claim 2, wherein said optical fiber comprises a single mode optical fiber.

4. An optical alignment system according to claim 1, further comprising a rigid mounting plate, fixedly attached to the X-ray imaging device, upon which said multi-axis positioner and said mirror are fixedly mounted.

5. An optical alignment system according to claim 1, wherein said second X-ray attenuating grid is adjustable in an X-Y plane of said second grid.

6. An optical alignment system according to claim 5, further comprising a locking mechanism to fix a position of said second grid in said X-Y plane.

7. An optical alignment system according to claim 5, said second grid is adjustable in said X-Y plane but fixed a preset Z distance from said first grid orthogonal to said X-Y plane.

8. An optical alignment system according to claim 7, wherein said first and second attenuating patterns correspond via the equation $D1=Z1/Z2*D2$.

9. An optical alignment system according to claim 5, said multi-axis positioner being three-axis adjustable in said X- and Y-directions and in a Z direction orthogonal to said X-Y plane of said second grid.

10. An optical alignment system according to claim 9, further comprising a locking mechanism coupled to said multi-axis positioner to fix said position of said visible-light point source with respect to said X-ray focal spot.

11. An optical alignment system according to claim 1, said first and second grids being attached to a common bracket removably but fixedly securable to the X-ray imaging device.

12. An optical alignment system according to claim 1, further comprising an X-ray detector, positionable below said first and second grids, adapted to detect a resultant pattern of X-rays transmitted through said first and second grids from the X-ray source.

13. An optical alignment system according to claim 12, further comprising a computer controller, coupled to said X-ray detector, automatically controlling a position of said second grid based on the X-rays detected by said detector.

14. An optical alignment system according to claim 12, further comprising:
   at least one electronic visible light detector, positionable below said second grid, adapted to detect a resultant intensity pattern of visible light transmitted through said first and second grids from said pellicle beamsplitter; and
   a computer controller, coupled to said X-ray detector, said visible light detector, and said multi-axis positioner, automatically controlling a position of said second grid based on the X-rays detected by said detector, and automatically controlling a position of said visible-light point source based on the visible light detected by said detector.

15. An optical alignment system according to claim 1, further comprising at least one electronic visible light detector, positionable below said first and second grids, adapted to detect a resultant intensity pattern of visible light transmitted through said first and second grids from said mirror.

16. An optical alignment system according to claim 15, further comprising a computer controller, coupled to said visible light detector and said multi-axis positioner, automatically controlling a position of said visible-light point source based on the visible light detected by said detector.

17. An optical alignment system according to claim 1, wherein said mirror comprises a pellicle beamsplitter.

18. A method for aligning a visible light alignment system and an X-ray imaging system of an X-ray imaging device, the X-ray imaging system having X-ray mirrors and an X-ray source having an X-ray focal spot, and the visible light alignment system having a visible light source, comprising the steps of:
   a) fixedly attaching two X-ray attenuating alignment grids a first distance apart from each other and a second distance apart from the X-ray focal spot, each grid having an attenuation pattern formed respectively therethrough to selectively block both X-rays and visible light;
   b) detecting a pattern of the X-rays from the X-ray source that pass through both alignment grids;

c) determining relative misalignment of the two alignment grids based on the resultant X-ray pattern detected in step b) and comparing it to the attenuation patterns of the two grids;

d) adjusting the position of one of the grids relative to the other grid so as to eliminate discrepancies between the detected X-ray pattern and the attenuation patterns of the grids;

e) when the recorded X-ray pattern is substantially identical to the attenuation grid patterns after iterating steps c) and d), activating the visible light source;

f) determining relative misalignment of the two alignment grids and the visible light source based on the resultant visible light pattern transmitted through the two grids; and g) adjusting the position of the visible light source so as to eliminate discrepancies between the transmitted visible light pattern and the attenuation patterns of the grid.

19. A method for aligning a visible light alignment system and an X-ray imaging system of an X-ray imaging device according to claim 18, wherein step b) further comprises the step of recording the resultant X-ray pattern, and wherein steps c) and d) are performed manually.

20. A method for aligning a visible light alignment system and an X-ray imaging system of an X-ray imaging device according to claim 18, wherein step f) further comprises the step of manually visually comparing the resultant visible light pattern and the attenuation patterns of the grids.

21. A method for aligning a visible light alignment system and an X-ray imaging system of an X-ray imaging device according to claim 20, wherein step g) further comprises the step of manually adjusting the position of the visible light source.

22. A method for aligning a visible light alignment system and an X-ray imaging system of an X-ray imaging device according to claim 18, wherein step f) further comprises the step of using at least one electronic visible light detector to detect the resultant visible light intensity pattern.

23. A method for aligning a visible light alignment system and an X-ray imaging system of an X-ray imaging device according to claim 18, further comprising the steps of:
   providing a digital X-ray detector to perform step b); and
   automatically performing step d) based on the resultant X-ray pattern detected by the digital X-ray detector.

24. A method for aligning a visible light alignment system and an X-ray imaging system of an X-ray imaging device according to claim 18, further comprising the steps of:
   providing an electronic visible light detector to detect the resultant visible light intensity pattern; and
   automatically performing step g) based on the resultant visible light intensity pattern detected by the visible light detector.

25. A method for aligning a visible light alignment system and an X-ray imaging system of an X-ray imaging device according to claim 18, further comprising the steps of:
   providing a digital X-ray detector to perform step b);
   automatically performing step d) based on the resultant X-ray pattern detected by the digital X-ray detector;
   providing a visible light detector to detect the resultant visible light intensity pattern; and
   automatically performing step g) based on the resultant visible light intensity pattern detected by the visible light detector.

* * * * *